(12) United States Patent
Kato et al.

(10) Patent No.: US 10,398,836 B2
(45) Date of Patent: Sep. 3, 2019

(54) CLAMPING DEVICE WITH STOP POINTS TO PREVENT EXCESS CLOSURE OF CLAMP

(71) Applicant: Nikkiso Company Limited, Tokyo (JP)

(72) Inventors: Ryo Kato, Shizuoka (JP); Shigeaki Funamura, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 15/665,635

(22) Filed: Aug. 1, 2017

(65) Prior Publication Data

US 2017/0326294 A1 Nov. 16, 2017

Related U.S. Application Data

(63) Continuation of application No. PCT/JP2016/053180, filed on Feb. 3, 2016.

(30) Foreign Application Priority Data

Feb. 3, 2015 (JP) .................................. 2015-018906

(51) Int. Cl.
*A61M 5/168* (2006.01)
*A61M 39/28* (2006.01)
(Continued)

(52) U.S. Cl.
CPC .......... *A61M 5/16813* (2013.01); *A61M 1/14* (2013.01); *A61M 5/16822* (2013.01);
(Continued)

(58) Field of Classification Search
CPC ........ A61M 39/28; A61M 39/283–285; A61M 5/16813; A61M 5/16822; A61M 5/14;
(Continued)

(56) References Cited

U.S. PATENT DOCUMENTS 3,419,245 A 12/1968 Scola
3,698,681 A 10/1972 Lacey
(Continued)

FOREIGN PATENT DOCUMENTS

EP 0637456 A1 2/1995
EP 2332611 A1 12/2009
(Continued)

OTHER PUBLICATIONS

International Search Report from the Japanese Patent Office for Application No. PCT/JP2015/067164, dated Jul. 14, 2015.
(Continued)

*Primary Examiner* — Nathan R Price
*Assistant Examiner* — Mark Alan Igel
(74) *Attorney, Agent, or Firm* — The Dobrusin Law Firm, P.C.; Daniel P. Aleksynas

(57) ABSTRACT

A clamping device comprising: a one end portion having a locked part at a tip and an other end portion having a locking part capable of locking the locked part, wherein the one end portion or the other end portion has an interfering part, and when the one end portion is further pressed with the locked part being locked by the locking part, the interfering part interferes with an appropriate part and prevents further movement of the locked part.

18 Claims, 8 Drawing Sheets

(51) Int. Cl.
*F16B 2/10* (2006.01)
*A61M 1/14* (2006.01)
*F16B 2/22* (2006.01)
*F16B 2/24* (2006.01)
*F16L 33/02* (2006.01)

(52) U.S. Cl.
CPC .......... *A61M 39/28* (2013.01); *A61M 39/284* (2013.01); *F16B 2/10* (2013.01); *F16B 2/22* (2013.01); *F16B 2/246* (2013.01); *F16L 33/021* (2013.01)

(58) Field of Classification Search
CPC .... A61M 1/14; F16K 7/04; F16K 7/07; F16K 7/075; F16K 7/068; F16K 7/065; F16K 7/061; F16K 7/066; F16K 7/063; F16K 7/0716; F16K 7/0693; F16B 2/10
USPC ...................................................... 251/9, 10
See application file for complete search history.

(56) References Cited

U.S. PATENT DOCUMENTS

| | | | |
|---|---|---|---|
| 3,822,052 A | 7/1974 | Lange | |
| 3,942,228 A * | 3/1976 | Buckman | A61M 39/284 251/4 |
| 4,053,135 A | 10/1977 | Saliaris | |
| 4,235,412 A | 11/1980 | Roth et al. | |
| 4,560,378 A * | 12/1985 | Weiland | A61M 5/00 251/8 |
| 4,589,626 A | 5/1986 | Kurtz et al. | |
| 4,643,389 A | 2/1987 | Elson et al. | |
| 5,035,399 A * | 7/1991 | Rantanen-Lee | A61M 39/28 251/10 |
| 5,203,056 A | 4/1993 | Funk et al. | |
| 5,238,218 A | 8/1993 | Mackal | |
| 6,113,062 A * | 9/2000 | Schnell | A61M 39/284 251/10 |
| 6,592,558 B2 | 7/2003 | Quah | |
| 6,698,681 B1 | 3/2004 | Guy et al. | |
| 8,262,639 B2 * | 9/2012 | Mathias | F16K 7/063 604/250 |
| 8,474,784 B2 * | 7/2013 | Kashmirian | A61M 39/284 251/10 |
| 2004/0089828 A1 | 5/2004 | Werth | |
| 2007/0261214 A1 | 11/2007 | Nerbonne | |
| 2010/0152681 A1 * | 6/2010 | Mathias | A61M 39/284 604/250 |
| 2010/0268161 A1 * | 10/2010 | Traversaz | A61M 5/14244 604/151 |
| 2012/0232497 A1 * | 9/2012 | Singh | A61M 39/284 604/250 |
| 2013/0310768 A1 * | 11/2013 | Ebara | A61M 5/168 604/250 |

FOREIGN PATENT DOCUMENTS

| | | | | |
|---|---|---|---|---|
| JP | S62-053667 A | 3/1987 | | |
| JP | H05-023792 B2 | 4/1993 | | |
| JP | 2001-353215 A | 12/2001 | | |
| JP | 2003-235971 | 8/2003 | | |
| JP | 2005-027721 | 2/2005 | | |
| JP | 2009-022744 | 2/2009 | | |
| JP | 2012-075520 | 4/2012 | | |
| JP | 4922246 B2 | 4/2012 | | |
| JP | WO 2012111310 A1 * | 8/2012 | | A61M 5/168 |
| JP | WO 2014021390 A1 * | 2/2014 | | A61M 5/162 |
| JP | WO 2015064233 A1 * | 5/2015 | | A61M 39/28 |
| WO | 03/063945 A1 | 8/2003 | | |
| WO | 2007/11500 A1 | 10/2007 | | |
| WO | 2011/035367 A1 | 3/2011 | | |
| WO | 2012/111310 A1 | 8/2012 | | |
| WO | WO 2013072199 A1 * | 5/2013 | | A61M 39/284 |
| WO | 2014/162376 | 9/2014 | | |

OTHER PUBLICATIONS

Written Opinion from the Japanese Patent Office for Application No. PCT/JP2015/067164, dated Jul. 14, 2015.
Potentially Related U.S. Appl. No. 15/392,748, filed Dec. 28, 2016.
International Search Report from the Japanese Patent Office for Application No. PCT/JP2016/053180, dated Apr. 26, 2016.
Extended European Search Report for Application No. PCT/JP2016/053180, dated Sep. 25, 2018.

* cited by examiner

CLAMPING DEVICE WITH STOP POINTS TO PREVENT EXCESS CLOSURE OF CLAMP

FIELD

The present teachings relates to a clamping device that clamps a flexible tube and intercepts the flow of a fluid at the clamped position.

BACKGROUND

In general, a blood circuit included in a dialysis apparatus or the like basically includes a flexible tube that allows a fluid, such as the blood of a patient, a physiological saline solution, or a drug to be given, used in a medical site to flow therethrough and connects various elements such as a dialyzer and an air-trap chamber to one another. A hitherto known clamping device for arbitrarily intercepting a desired position of such a flexible tube includes a one end portion having a first projection on the inner side thereof and a locked part at the tip thereof, an other end portion having a second projection at a position thereof facing the first projection and also having a locking part capable of locking the locked part, a middle portion continuous with the one end portion and with the other end portion, and an insertion hole allowing a flexible tube to be inserted between the first projection and the second projection (see PTL 1, for example).

When the one end portion is pressed and is brought closer to the other end portion, the locking part locks the locked part, whereby a clamped state is established. Furthermore, when the other end portion is bent, the locked part locked by the locking part can be unlocked, whereby an unclamped state is established. In the clamped state, the first projection and the second projection are positioned close to each other and thus clamp the flexible tube. Accordingly, the flow of the fluid (blood, a physiological saline solution, or the like) can be intercepted arbitrarily at the clamped position.

PATENT LITERATURE

PTL 1: Japanese Unexamined Patent Application Publication No. 2005-27721

SUMMARY

In the above known technique, however, if the one end portion is accidentally pressed further with the locked part being locked by the locking part, the locked part may be caught by an unintended part instead of the locking part. In such an event, the clamping device as a whole may be deformed, resulting in a problem in the clamping process to be performed thereafter. Moreover, an undesired position may be clamped, resulting in improper clamping.

The present teachings have been conceived in view of the above circumstances and provides a clamping device capable of clamping a flexible tube in a good manner without fail and also capable of intercepting the flow of a fluid in the flexible tube more exactly.

According to the present teachings, there is provided a clamping device including a one end portion having a first projection on an inner side and a locked part at a tip, an other end portion having a second projection at a position facing the first projection and a locking part capable of locking the locked part, a middle portion continuous with the one end portion and with the other end portion, and an insertion hole allowing a flexible tube to be inserted between the first projection and the second projection. A clamped state where the locked part is locked by the locking part is established when the one end portion is pressed and is brought closer to the other end portion, and an unclamped state is established when the locked part locked by the locking part is unlocked by bending the other end portion, the clamping device being configured to clamp the flexible tube in the clamped state where the first projection and the second projection are positioned close to each other and to intercept a flow of a fluid at a clamped position. The one end portion or the other end portion has an interfering part, and when the one end portion is further pressed with the locked part being locked by the locking part, the interfering part interferes with an appropriate part and prevents further movement of the locked part.

According to the present teachings, in the clamping device according to the teachings herein, the interfering part is a projection provided on the other end portion and near the locking part, and when the one end portion is further pressed with the locked part being locked by the locking part, the projection interferes with a predetermined point of the one end portion.

According to the present teachings, in the clamping device according to the teachings herein, the interfering part is a projection provided on the one end portion and near the locked part, and when the one end portion is further pressed with the locked part being locked by the locking part, the projection interferes with a predetermined point of the other end portion.

According to the present teachings, the clamping device according to the teachings herein further includes a positioning part capable of positioning, in a state where the flexible tube is clamped with the locked part being locked by the locking part, the first projection and the second projection relative to each other in a lengthwise direction of the flexible tube.

According to the present teachings, there is provided a medical circuit to which the clamping device according to any of the teachings herein.

According to the present teachings, the one end portion or the other end portion has the interfering part, and when the one end portion is further pressed with the locked part being locked by the locking part, the interfering part interferes with the appropriate part and prevents further movement of the locked part. Hence, the flexible tube can be clamped in a good manner without fail, and the flow of the fluid in the flexible tube can be intercepted more exactly.

According to the present teachings, the interfering part is the projection provided on the other end portion and near the locking part, and when the one end portion is further pressed with the locked part being locked by the locking part, the projection interferes with the predetermined point of the one end portion. Since the other end portion has the projection, the flexible tube can be clamped in a good manner without fail, and the flow of the fluid in the flexible tube can be intercepted more exactly.

According to the present teachings, the interfering part is the projection provided on the one end portion and near the locked part, and when the one end portion is further pressed with the locked part being locked by the locking part, the projection interferes with the predetermined point of the other end portion. Since the one end portion has the projection, the flexible tube can be clamped in a good manner without fail, and the flow of the fluid in the flexible tube can be intercepted more exactly.

According to the present teachings, the clamping device further includes the positioning part capable of positioning, in the state where the flexible tube is clamped with the locked part being locked by the locking part, the first projection and the second projection relative to each other in the lengthwise direction of the flexible tube. Hence, the sealing area can be minimized while the leakage of the fluid that may occur at the time of clamping is prevented. Furthermore, the clamping can be easily disabled.

According to the present teachings, the medical circuit can exert the advantageous effects exerted by the clamping device according to the teachings herein.

BRIEF DESCRIPTION

FIG. 1A includes a front perspective view of a clamping device according to a first embodiment of the present teachings.

FIG. 1B includes a rear perspective view of the clamping device of FIG. 1A.

DETAILED DESCRIPTION

Embodiments of the present teachings will now be described specifically with reference to the drawings.

Figure 1A:
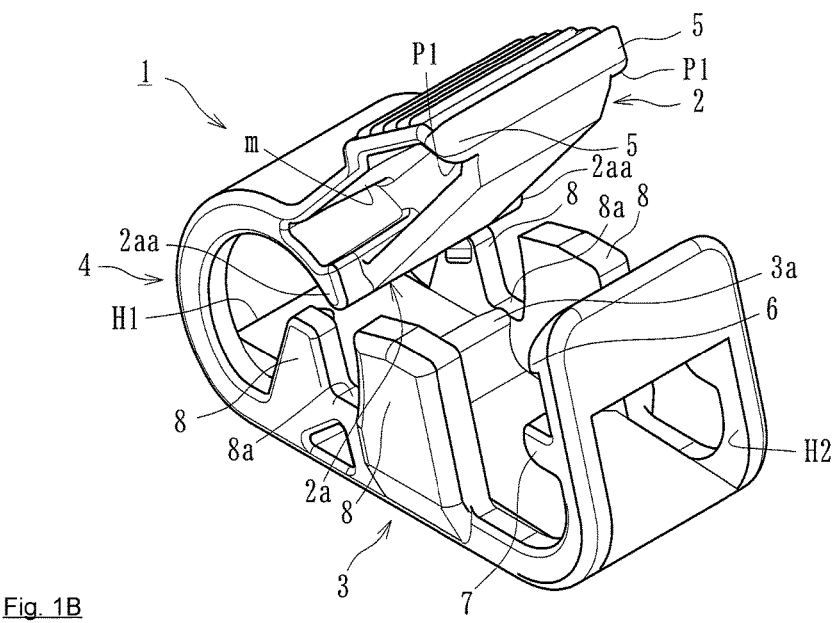
Figure 1B:
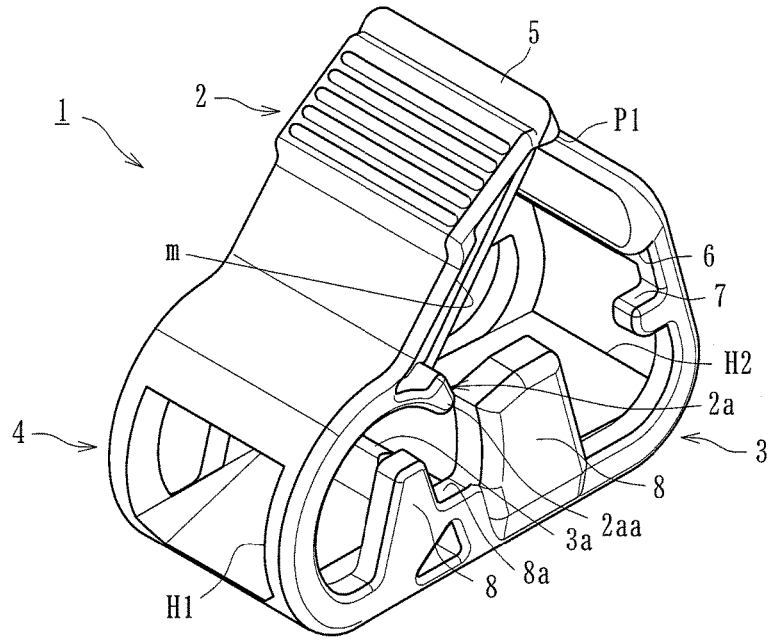
Figure 2:
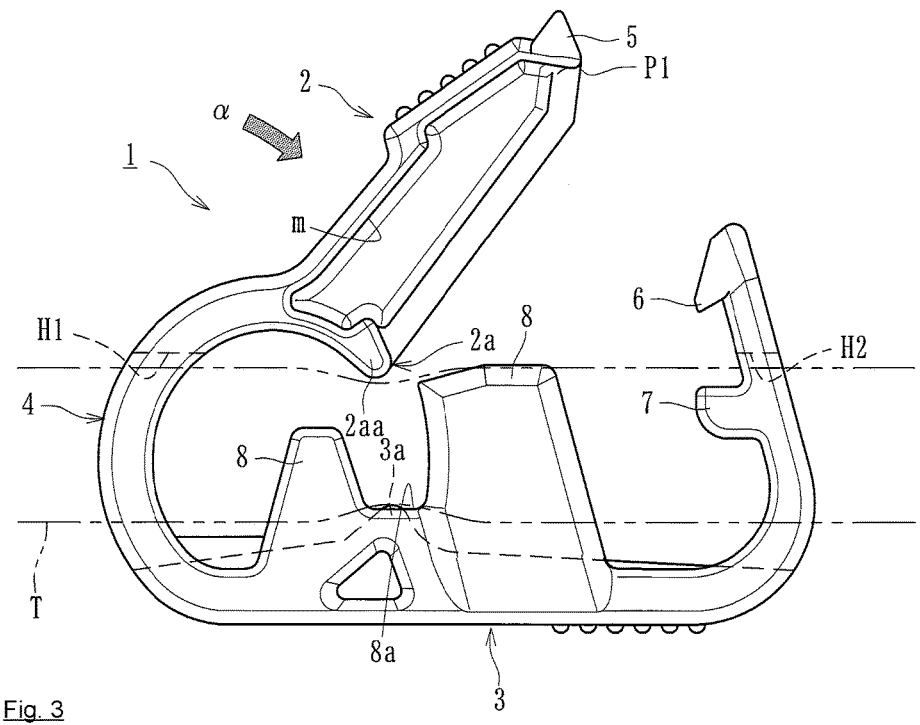
FIG. 2 is a side view of the clamping device (in an unclamped state).
Figure 3:
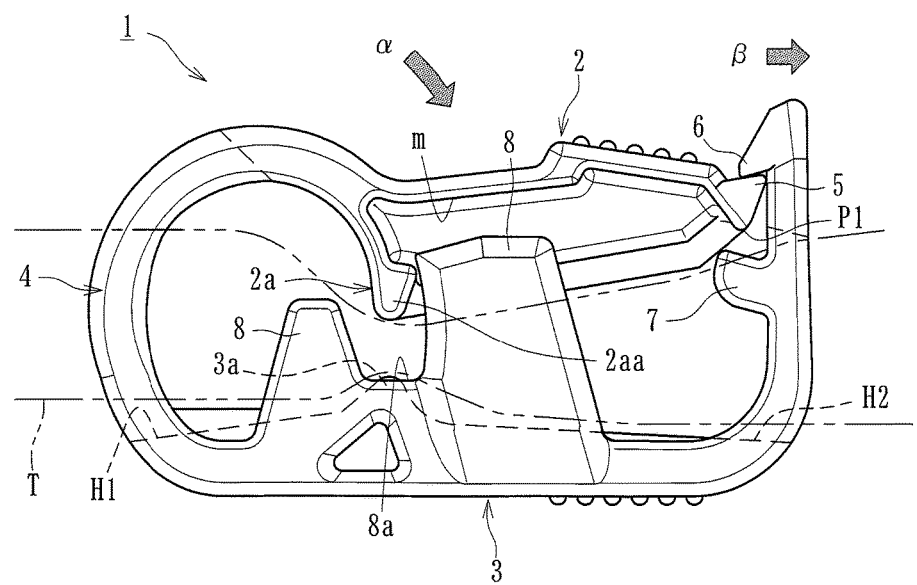
FIG. 3 is another side view of the clamping device (in a clamped state).

A clamping device 1 according to a first embodiment clamps a flexible tube and thus intercepts the flow of a fluid at the clamped position. As illustrated in FIGS. 1A to 4, the clamping device 1 basically includes a one end portion 2 having a first projection 2a, an other end portion 3 having a second projection 3a, and a middle portion 4 continuous with the one end portion 2 and with the other end portion 3. These portions are integrally formed of a predetermined resin (preferably, but not limited to, a thermoplastic resin moldable by extrusion (injection) molding or the like: for example, polypropylene, polyethylene, polyacetal, or the like). The clamping device 1 illustrated in FIGS. 1A, 1B and 2 is in an unclamped state. The clamping device 1 illustrated in FIG. 3 is in a clamped state.

The one end portion 2 includes the first projection 2a integrally formed on the inner surface (a surface facing the other end portion 3) thereof in such a manner as to project downward. The outer surface of the one end portion 2 has irregularities for preventing fingers of the worker from slipping thereon during the clamping work. The one end portion 2 further includes a locked part 5 provided at the tip thereof and being lockable by a locking part 6 to be described later. The other end portion 3 includes the second projection 3a integrally formed at a position facing the first projection 2a, and the locking part 6 integrally formed thereon and being capable of locking the locked part 5.

The middle portion 4 is a portion that is continuous with the one end portion 2 and with the other end portion 3 (a portion between the one end portion 2 and the other end portion 3) and has one insertion hole H1 into which a flexible tube T is to be inserted. Meanwhile, the other end portion 3 includes a part extending substantially linearly from the middle portion 4 (a part having the second projection 3a), and a part standing therefrom while being bent (a part having the locking part 6). The standing part has an other insertion hole H2 into which the flexible tube T is to be inserted.

As illustrated in FIG. 2, when the clamping device 1 according to the first embodiment is in the unclamped state where the tip of the one end portion 2 and the tip of the other end portion 3 are spaced apart from each other, the flexible tube T is inserted into the one insertion hole H1 and into the other insertion hole H2. Then, the one end portion 2 is pressed in a direction α indicated in FIG. 2, whereby the middle portion 4 is bent and the one end portion 2 is brought closer to the other end portion 3. Accordingly, as illustrated in FIG. 3, the locking part 6 locks the locked part 5, whereby the clamped state is established. In the clamped state, the first projection 2a and the second projection 3a are positioned close to each other and in combination clamp the flexible tube T extending through the insertion holes H1 and H2. Thus, the flow of the fluid can be intercepted at the clamped position.

In the clamped state illustrated in FIG. 3, when the other end portion 3 is bent in a direction β as indicated in FIG. 3, the locked part 5 locked by the locking part 6 is unlocked, whereby the unclamped state illustrated in FIG. 2 can be established. That is, when the locked part 5 locked by the locking part 6 is unlocked, the tip of the one end portion 2 and the tip of the other end portion 3 spontaneously move away from each other under the restoring force exerted by the resin material forming the clamping device 1. In the unclamped state, the first projection 2a and the second projection 3a are spaced apart from each other, and the clamping of the flexible tube T is disabled (the unclamped state).

The clamping device 1 according to the first embodiment further includes wall portions 8 integrally formed at two respective side edges of the other end portion 3. The wall portions 8 are a pair of wall-like members standing from the side edges of the other end portion 3 toward the one end portion 2 and can prevent the flexible tube T extending through the insertion holes H1 and H2 from moving in the radial direction thereof (any directions orthogonal to the lengthwise direction). To avoid the interference of the one end portion 2 with the wall portions 8 in the clamped state, the one end portion 2 has cuts m at two respective side edges thereof.

The wall portions 8 of the clamping device 1 according to the first embodiment have respective receiving parts 8a in the form of concave grooves that are open toward the one end portion 2. In the state illustrated in FIG. 3 where the locked part 5 is locked by the locking part 6 and the flexible tube (T) is thus clamped, the receiving parts 8a can receive respective fitting parts 2aa forming two respective end parts of the first projection 2a. That is, when the locked part 5 is locked by the locking part 6 and the fitting parts 2aa are fitted into the receiving parts 8a, the first projection 2a and the second projection 3a can be positioned relative to each other in the lengthwise direction of the flexible tube T.

The combination of the fitting parts 2aa and the receiving parts 8a according to the first embodiment corresponds to "the positioning part" according to the present teachings. In the state where the flexible tube (T) is clamped with the locked part 5 being locked by the locking part 6, the fitting parts 2aa and the receiving parts 8a can position the first projection 2a and the second projection 3a relative to each other in the lengthwise direction of the flexible tube (T) (i.e., a direction orthogonal to the direction in which the first projection 2a and the second projection 3a extend, or the lateral direction in FIG. 3).

With the positioning part formed of the fitting parts 2aa and the receiving parts 8a, the sealing area can be minimized while the leakage of the fluid that may occur at the time of clamping is prevented. Furthermore, the clamping can be easily disabled. In particular, the positioning part according to the first embodiment is formed of the fitting parts 2aa included in the one end portion 2 and the receiving parts 8a included in the other end portion 3, and the fitting parts 2aa are fitted into the receiving parts 8a when the locked part 5 is locked by the locking part 6, whereby the first projection 2a and the second projection 3a can be positioned relative to each other. Thus, the relative positioning of the first projection 2a and the second projection 3a in the lengthwise direction of the flexible tube (T) can be performed more exactly.

Furthermore, with the wall portions 8 standing from the side edges of the other end portion 3 and with the receiving parts 8a provided in the wall portions 8, the fitting into the receiving parts 8a can be performed more smoothly and more exactly. The wall portions 8 may extend from the side edges of the one end portion 2 toward the other end portion 3. In that case, the receiving parts in the form of concave grooves are provided in the wall portions 8, and the fitting parts to be fitted into the receiving parts are provided to the other end portion 3.

The pair of wall portions 8 according to the first embodiment stand from the two respective side edges of the one end portion 2 or the other end portion 3 and can guide the one end portion 2 when the locked part 5 is locked by the locking part 6. Since the clamping device 1 according to the first embodiment includes the positioning part (the fitting parts 2aa and the receiving parts 8a) and the wall portions 8, not only the relative positioning of the first projection 2a and the second projection 3a in the lengthwise direction of the flexible tube (T) but also the guiding of the one end portion 2 in the locking process can be implemented.

Figure 4:
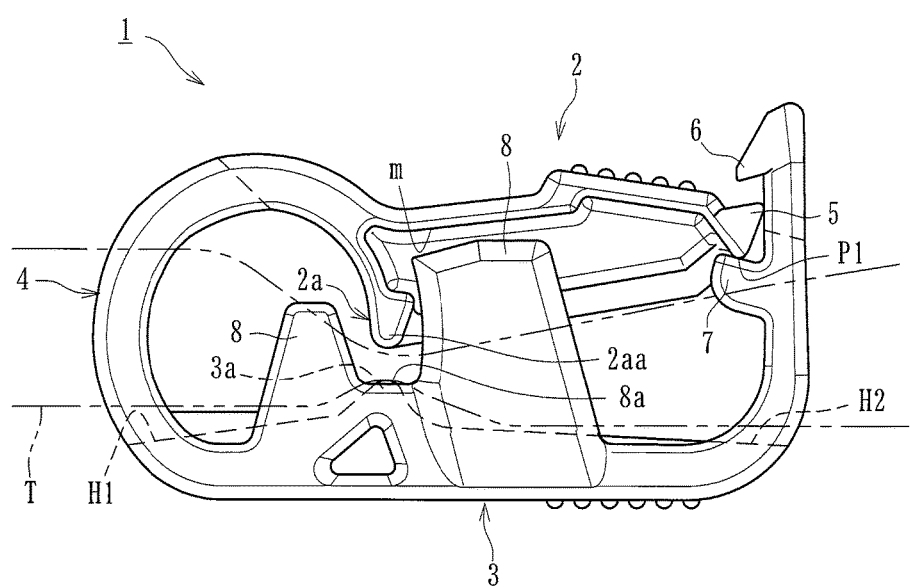
FIG. 4 is yet another side view of the clamping device (with an interfering part interfering with an appropriate part).

The other end portion 3 according to the first embodiment includes interfering parts 7 integrally formed thereon. The interfering parts 7 are each a projection integrally provided on the inner side at the tip of the other end portion 3 and near the locking part 6. When the one end portion 2 is further pressed in the direction α with the locked part 5 being locked by the locking part 6 (in the clamped state illustrated in FIG. 3), the interfering parts 7 interfere with respective predetermined points P1 of the one end portion 2 as illustrated in FIG. 4. Thus, the further movement of the locked part 5 can be prevented. The points with which the interfering parts 7 according to the first embodiment interfere are the two side edges at the tip of the one end portion 2 and on the back side of the locked part 5.

Figure 5:
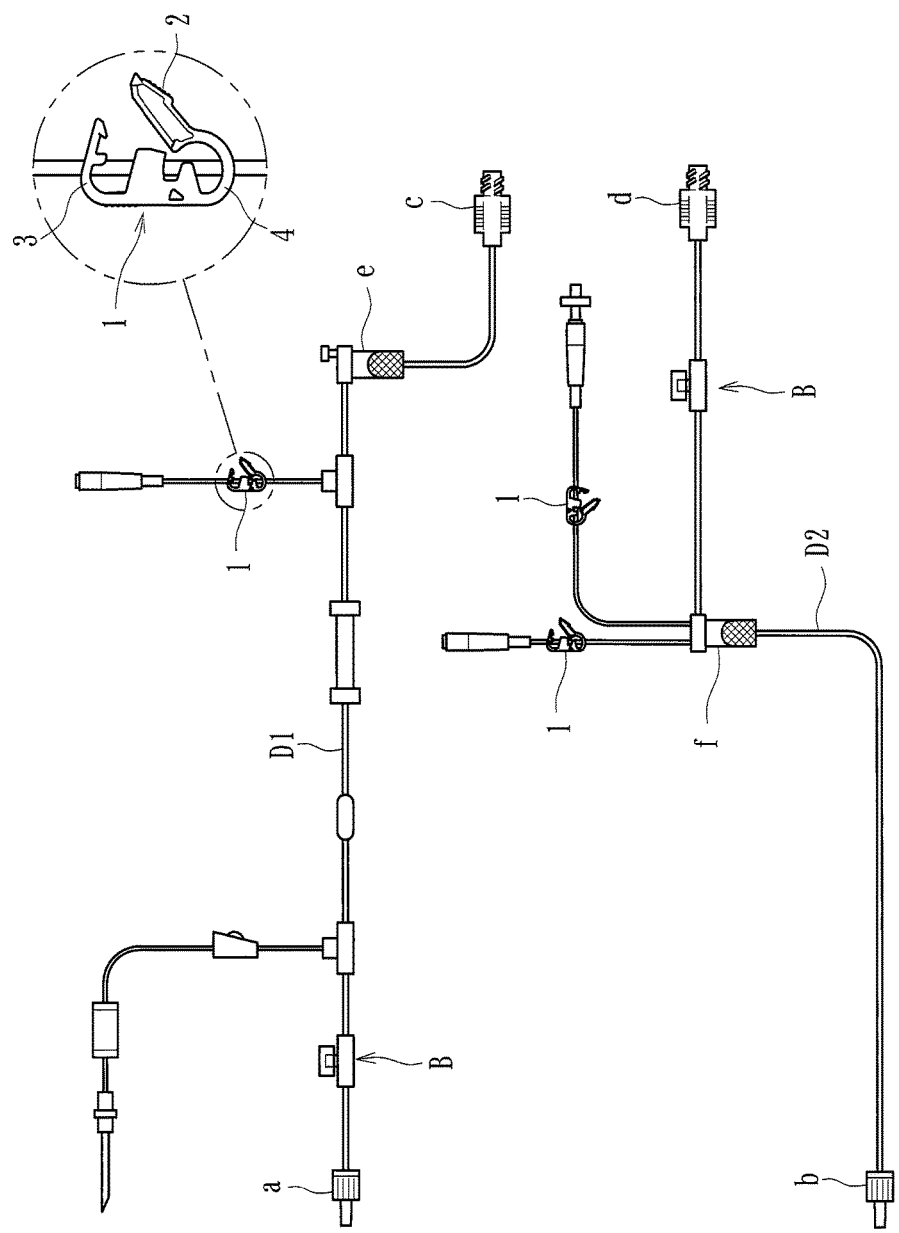
FIG. 5 is a schematic diagram of a medical circuit to which the clamping device is attached.

As illustrated in FIG. 5, the clamping device 1 according to the first embodiment is attached to a blood circuit (a medical circuit) including an arterial blood circuit D1 and a venous blood circuit D2 for extracorporeally circulating the blood of a patient. Specifically, the clamping device 1 is connected to any of flow routes in the arterial blood circuit D1 and the venous blood circuit D2 and flow routes branching off therefrom and is capable of intercepting the flow of the blood that is under extracorporeal circulation, a physiological saline solution, or the like. In FIG. 5, the clamping device 1 is attached to each of a flow route branching off from the arterial blood circuit D1, and flow routes extending from a venous air-trap chamber f connected to the venous blood circuit D2. The clamping device may be attached to any position but to flexible tubes forming the medical circuit.

The arterial blood circuit D1 is provided at the distal end thereof with a shunt connector (a) to which an arterial puncture needle is attachable. The arterial blood circuit D1 is further provided with an arterial air-trap chamber e at a halfway point thereof and with a dialyzer connector (c) at the proximal end thereof. The dialyzer connector (c) is connectable to an arterial connector of a blood purifier (a dialyzer). The venous blood circuit D2 is provided at the distal end thereof with a shunt connector (b) to which a venous puncture needle is attachable. The venous blood circuit D2 is further provided with the venous air-trap chamber (f) at a halfway point thereof and with a dialyzer connector d at the proximal end thereof. The dialyzer connector d is connectable to a venous connector of the blood purifier (the dialyzer). Reference character B denotes a rubber button (a coinfusing member) that allows a drug or the like to be infused into the flexible tube or the blood or the like to be collected from the flexible tube.

According to the first embodiment, the other end portion 3 includes the interfering parts 7. Furthermore, when the one end portion 2 is further pressed in the direction α with the locked part 5 being locked by the locking part 6, the interfering parts 7 interfere with the predetermined points P1 of the one end portion 2 and can prevent the further movement of the locked part 5. Therefore, the locked part 5 can be prevented from being caught by an unintended part instead of the locking part 6 when the flexible tube (T) is clamped. Hence, the flexible tube can be clamped in a good manner without fail, and the flow of the fluid in the flexible tube can be intercepted more exactly.

The interfering parts 7 according to the first embodiment are projections formed near the locking part 6 of the other end portion 3. When the one end portion 2 is further pressed in the direction α with the locked part 5 being locked by the locking part 6, the projections interfere with the predetermined points P1 of the one end portion 2. Since the other end portion 3 has such projections, the flexible tube can be clamped in a good manner without fail, and the flow of the fluid in the flexible tube (T) can be intercepted more exactly. Furthermore, as illustrated in FIG. 5, if the clamping device 1 according to the first embodiment is attached to a medical circuit, the medical circuit can exert the above advantageous effects exerted by the clamping device 1.

Now, a clamping device according to a second embodiment of the present teachings will be described.

Figure 6:
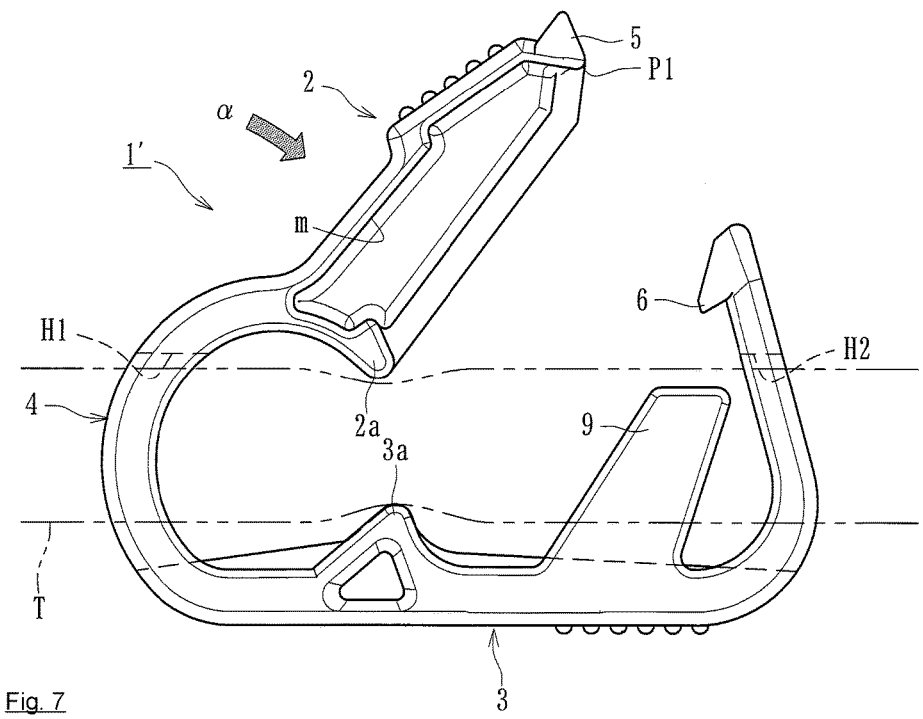
FIG. 6 is a side view of a clamping device (in an unclamped state) according to a second embodiment of the present teachings.
Figure 7:
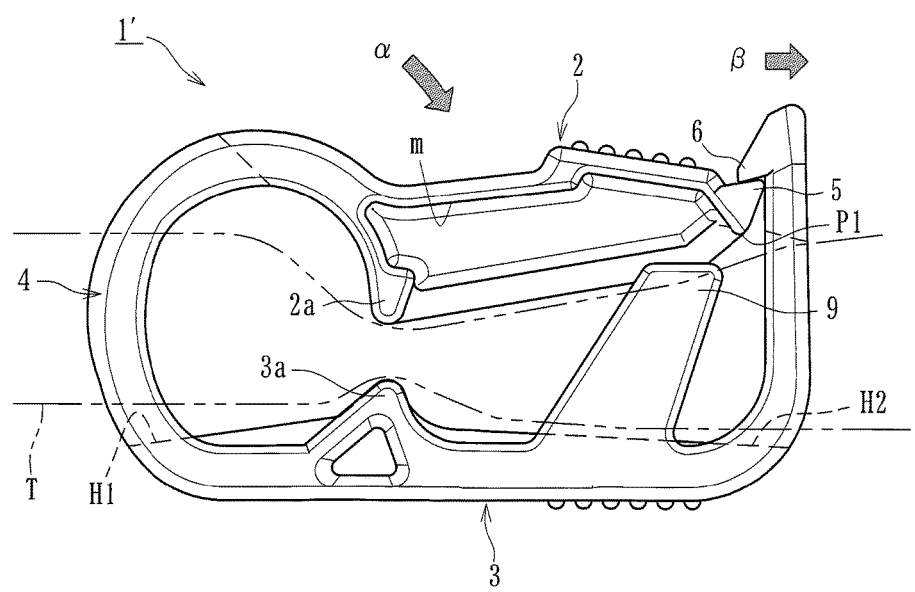
FIG. 7 is another side view of the clamping device (in a clamped state).
Figure 8:
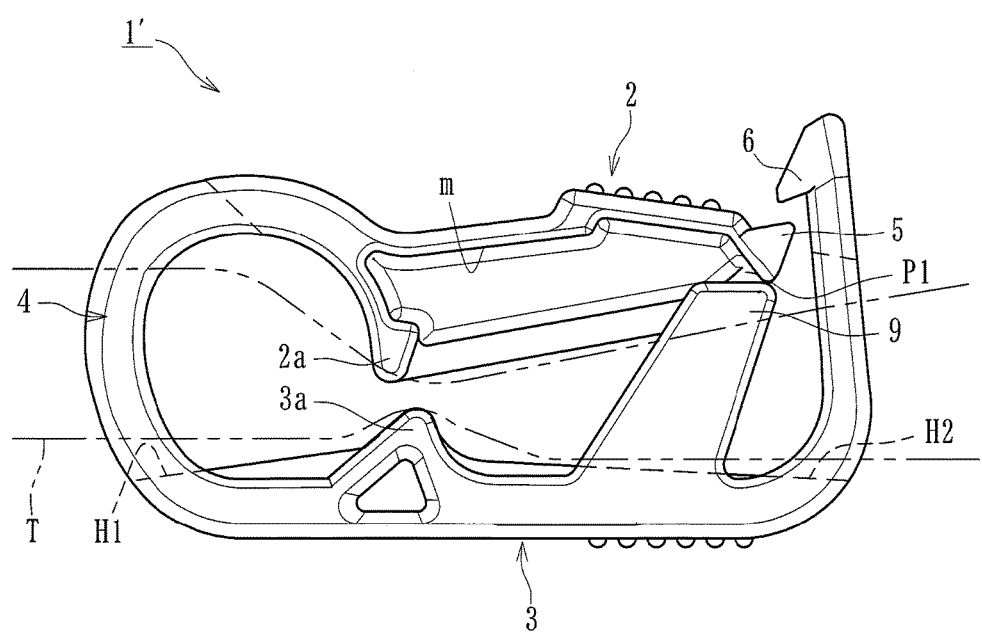
FIG. 8 is yet another side view of the clamping device (with an interfering part interfering with an appropriate part).

As with the case of the first embodiment, a clamping device 1' according to the second embodiment clamps a flexible tube and thus intercepts the flow of a fluid at the clamped position. As illustrated in FIGS. 6 to 8, the clamping device 1' basically includes the one end portion 2 having the first projection 2a, the other end portion 3 having the second projection 3a, and the middle portion 4 continuous with the one end portion 2 and with the other end portion 3. These portions are integrally formed of a predetermined resin (preferably, but not limited to, a thermoplastic resin moldable by extrusion (injection) molding or the like: for example, polypropylene, polyethylene, polyacetal, or the like). The clamping device 1' illustrated in FIG. 6 is in the unclamped state. The clamping device 1' illustrated in FIG. 7 is in the clamped state. Elements that are the same as those employed in the first embodiment are denoted by respective ones of the corresponding reference numerals, and detailed description of such elements is omitted.

As illustrated in FIG. 6, when the clamping device 1' according to the second embodiment is in the unclamped state where the tip of the one end portion 2 and the tip of the other end portion 3 are spaced apart from each other, the flexible tube (T) is inserted into the one insertion hole H1 and into the other insertion hole H2. Then, the one end portion 2 is pressed in the direction α as indicated in FIG. 6, whereby the middle portion 4 is bent and the one end portion 2 is brought closer to the other end portion 3. Accordingly, as illustrated in FIG. 7, the locking part 6 locks the locked part 5, whereby the clamped state is established. Furthermore, in the clamped state illustrated in FIG. 7, when the other end portion 3 is bent in the direction β as indicated in FIG. 7, the locked part 5 locked by the locking part 6 is unlocked. Thus, the unclamped state illustrated in FIG. 6 can be established.

The other end portion 3 according to the second embodiment includes interfering parts 9 integrally formed thereon. The interfering parts 9 are each a projection (a wall-like projection) integrally provided on the inner side of the other end portion 3 and near the second projection 3a. When the one end portion 2 is further pressed in the direction α with the locked part 5 being locked by the locking part 6 (in the clamped state illustrated in FIG. 7), the tips of the interfering parts 9 interfere with the respective predetermined points P1 of the one end portion 2 as illustrated in FIG. 8 and can prevent the further movement of the locked part 5. The points with which the interfering parts 9 according to the second embodiment interfere are the two side edges at the tip of the one end portion 2 and on the back side of the locked part 5.

According to the second embodiment, the other end portion 3 includes the interfering parts 9. Furthermore, when the one end portion 2 is further pressed in the direction α with the locked part 5 being locked by the locking part 6, the interfering parts 9 interfere with the predetermined points P1 of the one end portion 2 and can prevent the further movement of the locked part 5. Therefore, the locked part 5 can be prevented from being caught by an unintended part instead of the locking part 6 when the flexible tube (T) is clamped. Hence, the flexible tube can be clamped in a good manner without fail, and the flow of the fluid in the flexible tube can be intercepted more exactly.

The interfering parts 9 according to the second embodiment are projections formed near the second projection 3a of the other end portion 3. When the one end portion 2 is further pressed in the direction α with the locked part 5 being locked by the locking part 6, the projections interfere with the predetermined points P1 of the one end portion 2. Since the other end portion 3 has such projections, the flexible tube (T) can be clamped in a good manner without fail, and the flow of the fluid in the flexible tube can be intercepted more exactly. Furthermore, as illustrated in FIG. 5, if the clamping device 1' according to the second embodiment is attached to a medical circuit, the medical circuit can exert the above advantageous effects exerted by the clamping device 1'.

Now, a clamping device according to a third embodiment of the present teachings will be described.

Figure 9:
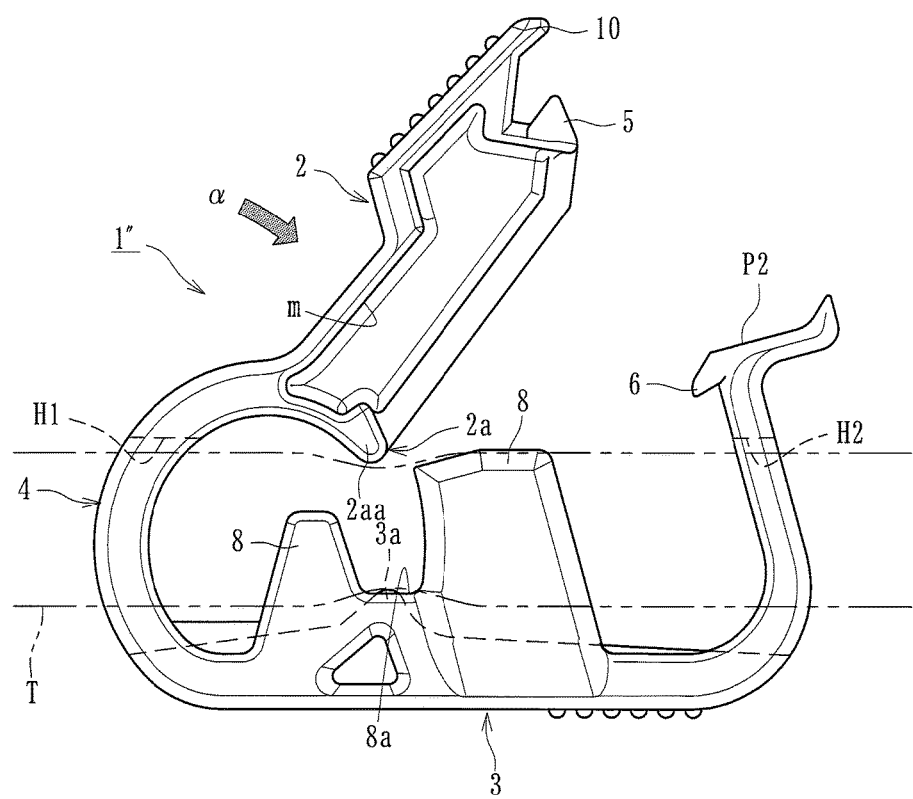
FIG. 9 is a side view of a clamping device (in an unclamped state) according to a third embodiment of the present teachings.
Figure 10:
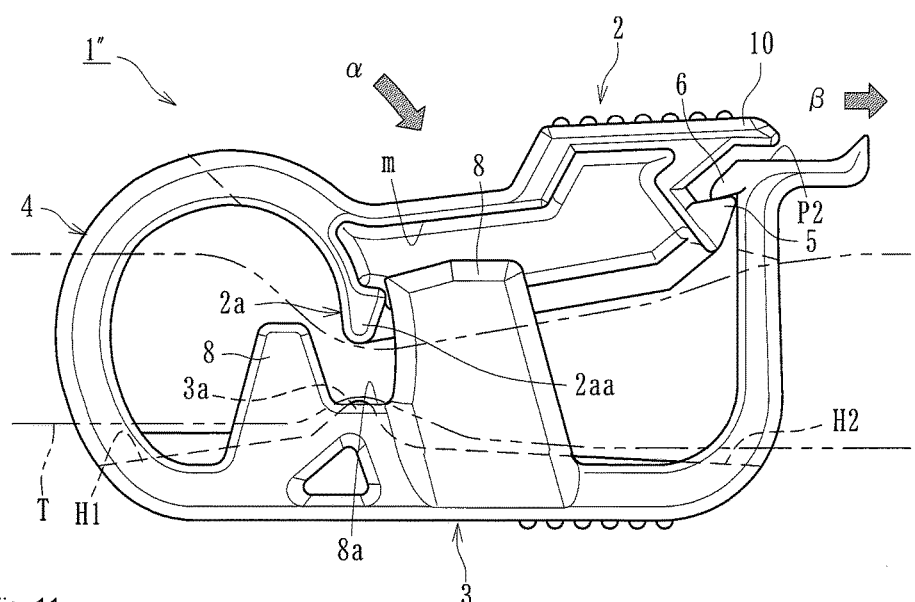
FIG. 10 is another side view of the clamping device (in a clamped state).
Figure 11:
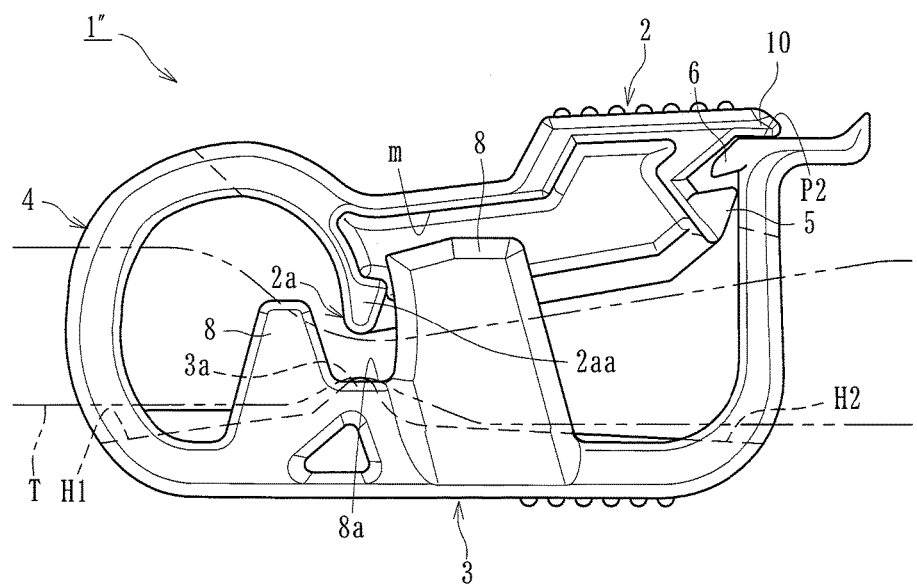
FIG. 11 is yet another side view of the clamping device (with an interfering part interfering with an appropriate).

As with the cases of the first and second embodiments, a clamping device 1" according to the third embodiment clamps a flexible tube and thus intercepts the flow of a fluid at the clamped position. As illustrated in FIGS. 9 to 11, the clamping device 1" basically includes the one end portion 2 having the first projection 2a, the other end portion 3 having the second projection 3a, and the middle portion 4 continuous with the one end portion 2 and with the other end portion 3. These portions are integrally formed of a predetermined resin (for example, polypropylene, olefinic resin, polyethylene, or the like). The clamping device 1" illustrated in FIG. 9 is in the unclamped state. The clamping device 1" illustrated in FIG. 10 is in the clamped state. Elements that are the same as those employed in the first embodiment are denoted by respective ones of the corresponding reference numerals, and detailed description of such elements is omitted.

As illustrated in FIG. 9, when the clamping device 1" according to the third embodiment is in the unclamped state where the tip of the one end portion 2 and the tip of the other end portion 3 are spaced apart from each other, the flexible tube (T) is inserted into the one insertion hole H1 and into the other insertion hole H2. Then, the one end portion 2 is pressed in the direction α as indicated in FIG. 9, whereby the middle portion 4 is bent and the one end portion 2 is brought closer to the other end portion 3. Accordingly, as illustrated in FIG. 10, the locking part 6 locks the locked part 5, whereby the clamped state is established. Furthermore, in the clamped state illustrated in FIG. 10, when the other end portion 3 is bent in the direction β as indicated in FIG. 10, the locked part 5 locked by the locking part 6 is unlocked. Thus, the unclamped state illustrated in FIG. 9 can be established.

The one end portion 2 according to the third embodiment includes an interfering part 10 integrally formed thereon. The interfering part 10 is a projection integrally provided at the tip of the one end portion 2 and near the locked part 5. When the one end portion 2 is further pressed in the direction α with the locked part 5 being locked by the locking part 6 (in the clamped state illustrated in FIG. 10), the interfering part 10 interferes with a predetermined point P2 of the other end portion 3 as illustrated in FIG. 11 and can prevent the further movement of the locked part 5. The point with which the interfering part 10 according to the third embodiment interferes is the tip of the other end portion 3 and on the side opposite the side having the locking part 6.

According to the third embodiment, the one end portion 2 includes the interfering part 10. Furthermore, when the one end portion 2 is further pressed in the direction α with the locked part 5 being locked by the locking part 6, the interfering part 10 interferes with the predetermined point P2 of the other end portion 3 and can prevent the further movement of the locked part 5. Therefore, the locked part 5 can be prevented from being caught by an unintended part instead of the locking part 6 when the flexible tube (T) is clamped. Hence, the flexible tube can be clamped in a good manner without fail, and the flow of the fluid in the flexible tube can be intercepted more exactly.

The interfering part 10 according to the third embodiment is a projection formed near the locked part 5 of the one end portion 2. When the one end portion 2 is further pressed in the direction α with the locked part 5 being locked by the locking part 6, the projection interferes with the predetermined point P2 of the other end portion 3. Since the one end portion 2 has such a projection, the flexible tube (T) can be clamped in a good manner without fail, and the flow of the fluid in the flexible tube can be intercepted more exactly. Furthermore, as illustrated in FIG. 5, if the clamping device 1″ according to the third embodiment is attached to a medical circuit, the medical circuit can exert the above advantageous effects exerted by the clamping device 1″.

In the third embodiment, as in the first embodiment, when the locked part 5 is locked by the locking part 6 and the fitting parts 2*aa* are fitted into the respective receiving parts 8*a*, the first projection 2*a* and the second projection 3*a* can be positioned relative to each other in the lengthwise direction of the flexible tube (T). With the positioning part formed of the fitting parts 2*aa* and the receiving parts 8*a*, the sealing area can be minimized while the leakage of the fluid that may occur at the time of clamping is prevented. Furthermore, the clamping can be easily disabled.

While some embodiments have been described above, the present teachings is not limited thereto. For example, the other end portion 3 may include no wall portions 8. Instead, the one end portion 2 may include wall portions corresponding to the wall portions 8. Moreover, the position, the shape, and the length of projection of the locking part 6 and the position, the shape, and other factors of the locked part 5 may be set arbitrarily. Furthermore, the position, the shape, and other factors of each interfering part may be set arbitrarily. The medical circuit to which the clamping device according to the present teachings is to be attached is not limited to a blood circuit and may be any of various medical circuits including flexible tubes.

The present teachings are applicable to any clamping devices having different external shapes, any additional functions, and so forth, as long as the following holds true: the clamping devices each include the interfering part provided on the one end portion or on the other end portion; and when the one end portion is further pressed with the locked part being locked by the locking part, the interfering part interferes with an appropriate part and can prevent the further movement of the locked part.

REFERENCE SIGN LIST

1, 1', 1″ clamping device
2 one end portion
2*a* first projection
2*aa* fitting part (positioning part)
3 other end portion
3*a* second projection
4 middle portion
5 locked part
6 locking part
7 interfering part
8 wall portion
8*a* receiving part (positioning part)
9 interfering part
10 interfering part
T flexible tube
H1, H2 insertion hole

The invention claimed is:

1. A clamping device comprising:
   a one end portion having:
      a first projection on an inner side, and
      a locked part at a tip;
   an other end portion having:
      a second projection at a position facing the first projection, and
      a locking part capable of locking the locked part;
   a middle portion continuous with the one end portion and with the other end portion; and
   an insertion hole allowing a flexible tube to be inserted between the first projection and the second projection,
   wherein a clamped state where the locked part is locked by the locking part is established when the one end portion is pressed and is brought closer to the other end portion, and an unclamped state is established when the locked part locked by the locking part is unlocked by bending the other end portion, the clamping device being configured to clamp the flexible tube in the clamped state where the first projection and the second projection are positioned close to each other and to intercept a flow of a fluid at a clamped position;
   wherein the other end portion has an interfering part that is a projection provided on the other end portion and near the locking part, and when the one end portion is further pressed with the locked part being locked by the locking part, the interfering part interferes with at least one side edge at the tip of the one end portion and on a back side of the locked part; and
   wherein the clamping device comprises a lengthwise direction from the insertion hole to the locking part, wherein the interfering part projects from the other end portion along the lengthwise direction.

2. The clamping device according to claim 1, further comprising a positioning part capable of positioning, in a state where the flexible tube is clamped with the locked part being locked by the locking part, the first projection and the second projection relative to each other in the lengthwise direction of the flexible tube.

3. The clamping device according to claim 2, further comprising at least one pair of walls integrally formed along opposing side edges of the one end extending toward the other end or at least one pair of walls integrally formed along opposing side edges of the other end extending toward the one end, wherein a fitting part of the positioning part is received in a receiving portion of the positioning part formed within the at least one pair of walls during a clamping operation.

4. The clamping device according to claim 2, wherein a fitting part of the positioning part is located near, and integrally formed with, a first end of the first projection, an opposing second end of the first projection, or both.

5. The clamping device according to claim 2, wherein the positioning part includes one or more fitting parts and one or more receiving parts, and the one or more receiving parts are configured to receive the one or more fitting parts.

6. A medical circuit to which the clamping device according to claim 1 is attached.

7. The medical circuit according to claim 6, wherein the clamping device further comprises a positioning part capable of positioning, in a state where the flexible tube is clamped with the locked part being locked by the locking part, the first projection and the second projection relative to each other in the lengthwise direction of the flexible tube.

8. The clamping device according to claim 1, further comprising at least one pair of walls integrally formed along opposing side edges of the other end extending toward the one end and positioned adjacent to the insertion hole.

9. The clamping device according to claim 8, wherein a width between walls of the at least one pair of walls located on opposing side edges of the other end is greater than a width of the locked part so that, when in the clamped state, the one end is positioned between the at least one pair of walls.

10. The clamping device according to claim 9, further comprising a positioning part capable of positioning, in a state where the flexible tube is clamped with the locked part being locked by the locking part, the first projection and the second projection relative to each other in the lengthwise direction of the flexible tube.

11. A medical circuit to which the clamping device according to claim 10 is attached.

12. The clamping device according to claim 8, wherein the at least one pair of walls is the interfering part.

13. The clamping device according to claim 1, further comprising at least one pair of walls integrally formed along opposing side edges of the one end extending toward the other end and positioned adjacent to the insertion hole.

14. The clamping device according to claim 13, further comprising a positioning part capable of positioning, in a state where the flexible tube is clamped with the locked part being locked by the locking part, the first projection and the second projection relative to each other in the lengthwise direction of the flexible tube.

15. The clamping device according to claim 13, wherein a width between walls of the at least one pair of walls located on opposing side edges of the one end is greater than a width of the locked part so that, when in the clamped state, the other end is positioned between the at least one pair of walls.

16. The clamping device according to claim 13, wherein the at least one pair of walls is the interfering part.

17. The clamping device according to claim 1, wherein an outer surface of the one end portion, the other end portion, or both include one or more irregularities to increase friction on the outer surface.

18. The clamping device according to claim 1, wherein the interference part is positioned between the locking part and the insertion hole.

* * * * *